United States Patent [19]

Makisumi et al.

[11] 4,183,856
[45] Jan. 15, 1980

[54] PROCESS FOR THE PRODUCTION OF UREA DERIVATIVES

[75] Inventors: Yasuo Makisumi, Kawanishi; Takashi Sasatani, Sakai; Akira Murabayashi, Ibaraki, all of Japan

[73] Assignee: Shionogi & Co., Ltd., Osaka, Japan

[21] Appl. No.: 895,105

[22] Filed: Apr. 10, 1978

[30] Foreign Application Priority Data

Apr. 28, 1977 [JP] Japan .................. 52-49629

[51] Int. Cl.² .......................... C07D 261/14
[52] U.S. Cl. ...................... 548/246; 548/196; 548/214; 546/306
[58] Field of Search ............ 260/307 H, 305, 306.8 R, 260/295 E, 553 A, 306.8 A

[56] References Cited

U.S. PATENT DOCUMENTS

| | | | |
|---|---|---|---|
| 2,755,285 | 7/1956 | O'Neill et al. | 260/306.8 R |
| 2,756,135 | 7/1956 | Searle | 260/305 |
| 3,293,257 | 12/1966 | Woods et al. | 260/295 E |
| 3,547,940 | 12/1970 | Brantleeg | 260/307 H |
| 3,734,923 | 5/1973 | Dowding et al. | 260/306.8 R |
| 3,755,347 | 8/1973 | Guillot et al. | 260/306.8 R |
| 4,013,706 | 3/1977 | Anatol | 260/553 A |
| 4,028,376 | 6/1977 | Yukinaga et al. | 260/307 H |
| 4,046,770 | 9/1977 | Paget et al. | 260/305 |
| 4,062,861 | 12/1977 | Yukinaga et al. | 260/307 H |

FOREIGN PATENT DOCUMENTS

| | | | |
|---|---|---|---|
| 1209801 | 1/1966 | Fed. Rep. of Germany | 260/305 |
| 6605902 | 1/1966 | Netherlands | 260/306.8 A |
| 6811320 | 2/1969 | Netherlands | 260/306.8 A |

OTHER PUBLICATIONS

Thomas; Anhydrous Aluminium Chloride in Organic Chemistry; (1941) p. 382.

Primary Examiner—Donald G. Daus
Assistant Examiner—Mary C. Lee
Attorney, Agent, or Firm—Wenderoth, Lind & Ponack

[57] ABSTRACT

Urea derivatives of the formula

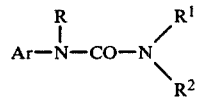

(wherein Ar represents a residue of 5- or 6-membered heteroaromatic ring; R represents a hydrogen atom or a $C_1$-$C_6$ alkyl group; $R^1$ represents a $C_1$-$C_6$ alkyl group; and $R^2$ represents a $C_1$-$C_6$ alkyl, $C_2$-$C_6$ alkenyl, or $C_1$-$C_6$ alkoxy group) are produced by reacting an amine of the formula

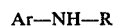

(wherein Ar and R have the significance given above) with a carbamoyl halogenide of the formula

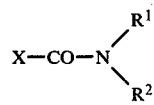

(wherein X represents a halogen atom, and $R^1$ and $R^2$ have the significance given above) in the presence of a Lewis acid in an inert solvent.

7 Claims, No Drawings

PROCESS FOR THE PRODUCTION OF UREA DERIVATIVES

The present invention relates to a novel process for the production of urea derivatives of the formula

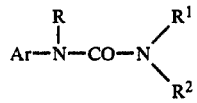

(wherein Ar represents a residue of 5- or 6-membered heteroaromatic ring; R represents a hydrogen atom or a $C_1$-$C_6$ alkyl group; $R^1$ represents a $C_1$-$C_6$ alkyl group; and $R^2$ represents a $C_1$-$C_6$ alkyl, $C_2$-$C_6$ alkenyl, or $C_1$-$C_6$ alkoxy group).

Heteroaromatic urea derivatives are useful as selective herbicides. For example, 5-alkylisoxazolylureas are disclosed in U.S. Pat. No. 4,062,861 and N-substituted 1-(2-benzothiazolyl)ureas are disclosed in Netherland Pat. Pub. No. 7,211,273. However, the known processes for the production of these urea derivatives are less satisfactory for industrial purposes. For example, said U.S. Patent discloses a preparative process of 1,1-dimethyl-3-(5-t-butyl-3-isoxazolyl)urea which comprises reacting 3-amino-5-t-butylisoxazole with N,N-dimethylcarbamoyl chloride in the presence of a base such as pyridine. This preparation has such a defect that said product yield inevitably lowers due to formation of 1,3-bis(5-t-butyl-3-isoxazolyl)urea as an undesirable by-product.

After diligent investigation for developing an improved process for the production of said urea derivatives (I) free from such by-products, the present inventors have found out that by using a Lewis acid in the above reaction system, the reaction selectively runs to give the highest yield and the availability of starting amines, Ar—NH—R (II), can be applied up to that of less reactive heteroaromatic amines. Then, the present invention has been successfully reduced to practice.

The present invention relates to a process for the production of urea derivatives of the formula

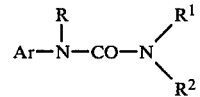

(wherein Ar represents a residue of 5- or 6-membered heteroaromatic ring, R represents a hydrogen atom or a $C_1$-$C_6$ alkyl group; $R^1$ represents a $C_1$-$C_6$ alkyl group; and $R^2$ represents a $C_1$-$C_6$ alkyl, $C_2$-$C_6$ alkenyl, or $C_1$-$C_6$ alkoxy group) which comprises reacting an amine of the formula

Ar—NH—R   (II)

(wherein Ar and R have the significance given above) with a carbamoyl halogenide of the formula

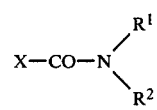

(wherein X represents a halogen atom, and $R^1$ and $R^2$ have the significance given above) in the presence of a Lewis acid in an inert solvent.

The definition of the above substituents can be complemented in the following description: the heteroaromatic ring involves 3-isoxazolyl (e.g. 5-alkyl-3-isoxazolyl, 5-phenyl-3-isoxazolyl), 2-thiazolyl (e.g. 4-alkyl-2-thiazolyl, 4,5-dialkyl-2-thiazolyl), 3-isothiazolyl (e.g. 5-phenyl-3-isothiazolyl), 2-benzothiazolyl, and 2-pyridyl rings; the alkyl group involves methyl, ethyl, propyl, i-propyl, butyl, i-butyl, t-butyl, pentyl, and i-pentyl; the alkenyl group includes allyl, butenyl, pentenyl, and hexenyl; the alkoxy group includes methoxy, ethoxy, propoxy, and butoxy; the halogen implies chlorine, bromine, and iodine; and the Lewis acid implies aluminum chloride, stannic chloride, titanium tetrachloride, magnesium chloride, and zinc chloride.

Said reaction in this invention can be carried out in the presence of a Lewis acid in a suitable inert solvent (e.g. benzene, toluene, xylene, chloroform, methylene chloride, dichloroethane, trichloroethylene), under heating at preferably around the boiling point of the solvent. Amount of the carbamoyl halogenide (III) to the starting amine (II) can be adjusted to about 1.0 to about 1.2 molar equivalent, preferably about 1.0 to about 1.1 molar equivalent. Ratio of the Lewis acid to the starting amine (II) can be about 1.0 to about 1.2 molar equivalent, preferably about 1.0 to about 1.1 molar equivalent.

The industrial advantage of the present invention over the prior arts is as follows:

(1) said reaction affords only the objective pure product in an almost quantitative yield without significant side reactions;

(2) the applicable scope of said reaction is wide enough to be applied to various less reactive heteroaromatic amines; and (3) the operation is simple, and the final product can be easily isolated and purified.

Presently-preferred and practical embodiments of the present invention are illustratively shown in the following examples.

EXAMPLE 1

N,N-Dimethylcarbamoyl chloride (7.91 g) and aluminum chloride (9.80 g) are added to toluene (100 ml), and the mixture is stirred at room temperature for 30 minutes. To this mixture is added 3-amino-5-t-butylisoxazole (9.81 g), and the resulting mixture is refluxed for 6 hours with stirring. After cooling, the reaction mixture is mixed with water, stirred at room temperature and shaken with toluene. The organic layer is evaporated to remove the toluene, whereby 1,1-dimethyl-3-(5-t-butyl-3-isoxazolyl)urea (14.63 g) is obtained. Yield is 98.9%. Melting point of the colorless crystalline product is 119 to 120.5° C. (after recrystallization from benzene).

EXAMPLES 2-5

Using the following Lewis acids instead of aluminum chloride, the reaction is carried out as in above Example 1, whereby 1,1-dimethyl-3-(5-t-butyl-3-isoxazolyl)urea is obtained in the respective yields as shown in Table 1.

Table 1

| Ex. No. | Lewis acid | Yield (%) |
| --- | --- | --- |
| 2 | SnCl$_4$ | 99.1 |
| 3 | TiCl$_4$ | 98.8 |

| Ex. No. | Lewis acid | Yield (%) |
| --- | --- | --- |
| 4 | MgCl₂ | 97.4 |
| 5 | ZnCl₂ | 97.4 |

EXAMPLES 6–12

Using the following starting materials (II) and (III), the reaction is effected as in Example 1, whereby the corresponding urea derivatives (I) are obtained as shown in Table 2.

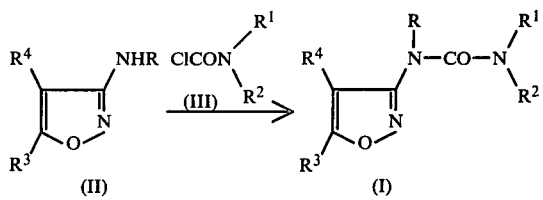

Table 2

| Ex. No. | II | | | III | | I | Yield (%) |
| --- | --- | --- | --- | --- | --- | --- | --- |
| | R | R³ | R⁴ | R¹ | R² | m.p. (°C.) or b.p. (°C.)/mmHg | |
| 6 | H | Me | H | Me | Me | 153–154 | 97.3 |
| 7 | H | Et | H | Me | Me | 87.5–89 | 98.4 |
| 8 | H | i-Pr | H | Me | Me | 69.5–71 | 98.0 |
| 9 | Et | Me | H | Me | Me | 105–107/0.2 | 95.9 |
| 10 | Me | t-Bu | H | Me | Me | 93–94 | 97.7 |
| 11 | Me | Ph | H | Me | Me | 165–168/0.4 | 97.2 |
| 12 | H | t-Bu | Br | Me | Me | 169.5–171 | 96.8 |

Note) The abbreviations in Table 2 have the following significances:
H (hydrogen), Me (methyl group), Et (ethyl group), Pr (propyl group), Bu (butyl group), Ph (phenyl group), Br (bromine), i- (iso-), t- (tertiary-)

EXAMPLE 13

N,N-Dimethylcarbamoyl chloride (1.29 g) and aluminum chloride (1.60 g) are dissolved in toluene (40 ml), and the mixture is stirred at room temperature for 30 minutes. To this mixture is added 3-amino-5-phenylisothiazole (1.76 g), and the resulting mixture is refluxed for 6 hours with stirring. After cooling, the reaction mixture is mixed with water and shaken with toluene. The organic layer is separated, washed with water, dried, and concentrated to dryness to give 1,1-dimethyl-3-(5-phenyl-3-isothiazolyl)urea (2.38 g). Yield is 96.4%. Melting point of the colorless crystals is 129 to 130.5° C. (after recrystallization from benzene/petroleum benzin).

EXAMPLE 14

A mixture of 2-amino-4-methylthiazole (1.14 g), N,N-dimethylcarbamoyl chloride (1.29 g), aluminum chloride (1.60 g), and xylene (40 ml) is refluxed for 20 hours. The reaction mixture is worked up as in Example 1, whereby 1,1-dimethyl-3-(4-methyl-2-thiazolyl)urea (1.73 g) is obtained. Yield is 93.5%. Melting point is 97° to 98° C. (Pure product is recrystallized from ether/petroleum ether).

EXAMPLE 15

Using 2-amino-4,5-dimethylthiazole (1.28 g), N,N-dimethylcarbamoyl chloride (1.29 g), aluminum chloride (1.60 g), and xylene (40 ml), the reaction is run as in Example 1, whereby 1,1-dimethyl-3-(4,5-dimethyl-2-thiazolyl)urea (1.82 g) is obtained. Yield is 91.5%. Melting point is 202.5° to 204° C. (after recrystallization from ethyl acetate).

EXAMPLE 16

Using 2-aminobenzothiazole (1.50 g), N,N-dimethylcarbamoyl chloride (1.29 g), aluminum chloride (1.60 g), and trichloroethylene (40 ml), the reaction is effected as in Example 1, except that the reflux is carried out for 40 hours. Thus, 1,1-dimethyl-3-(2-benzothiazolyl)urea (2.16 g) is obtained. Yield is 97.7%. Melting point is higher than 300° C. (after recrystallization from ethanol).

EXAMPLE 17

A mixture of 2-aminopyridine (941 mg), aluminum chloride (1.60 g), and xylene (30 ml) is heated under reflux for 8 hours. After cooling, the reaction mixture is made alkaline with sodium hydroxide and shaken with chloroform. The organic layer is separated, washed with water, dried, and evaporated to remove the solvent, whereby 1,1-dimethyl-3-(2-pyridyl)-urea (1.57 g) is obtained as an oily product. The picrate of this product shows a melting point of 187° to 189.5° C. (decomp.).

EXAMPLE 18

Using 3-amino-5-t-butylisoxazole and N-ethyl-N-methylcarbamoyl chloride, the reaction is carried out as in Example 1, whereby 1-ethyl-1-methyl-3-(5-t-butyl-3-isoxazolyl)urea is obtained. Yield is 96.1%. Melting point is 88.5° to 89.5° C.

EXAMPLE 19

Using 3-amino-5-t-butylisoxazole and N-allyl-N-methylcarbamoyl chloride, the reaction is effected as in Example 1, whereby 1-allyl-1-methyl-3-(5-t-butyl-3-isoxazolyl)urea is obtained. Yield is 90.5%. Melting point is 90.0° to 91.0° C.

EXAMPLE 20

Using 3-amino-5-t-butylisoxazole and N-methoxy-N-methylcarbamoyl chloride, the reaction is run as in Example 1, whereby 1-methoxy-1-methyl-3-(5-t-butyl-3-isoxazolyl)urea is obtained. Yield is 94.7%. Melting point is 106.0° to 107.0° C.

EXAMPLE 21

Using 3-amino-5-t-butylisoxazole and N,N-diethylcarbamoyl chloride, the reaction is effected as in Example 1, whereby 1,1-diethyl-3-(5-t-butyl-3-isoxazolyl)urea is obtained. Yield is 98.2%. Melting point is 122.0° to 123.5° C.

What is claimed is:

1. A process for the production of a compound of the formula:

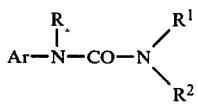

wherein Ar represents a member selected from the group consistng of (a) 3-isoxazolyl, (b) 2-thiazolyl, (c) 3-isothiazolyl, (d) 2-benzothiazolyl, (e) 2-pyridyl and (f) one of said groups (a) to (e) substituted by one or two substituents selected from the group of methyl, ethyl, propyl, i-propyl, butyl, i-butyl, t-butyl, pentyl, i-pentyl and phenyl; R represents hydrogen or $C_1$–$C_6$ alkyl; $R^1$ represents $C_1$–$C_6$ alkyl; and $R^2$ represents $C_1$–$C_6$ alkyl, $C_2$–$C_6$ alkenyl or $C_1$–$C_6$ alkoxy, which is characterized by reacting an amine of the formula:

Ar—NH—R wherein Ar and R are as defined above with a carbonyl halogenide of the formula:

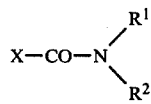

wherein X represents a halogen atom and $R^1$ and $R^2$ are as defined above in the presence of a Lewis acid in an inert solvent.

2. A process according to claim 1, in which Ar is selected from the group consisting of
5-methyl-3-isoxazolyl,
5-ethyl-3-isoxazolyl,
5-propyl-3-isoxazolyl,
5-t-butyl-3-isoxazolyl,
5-phenyl-3-isoxazolyl,
4-bromo-5-t-butyl-3-isoxazolyl,
5-phenyl-3-isothiazolyl,
4-methyl-2-thiazolyl,
4,5-dimethyl-2-thiazolyl,
2,benzthiazolyl, and
2-pyridyl.

3. Process according to claim 1, wherein the reaction is carried out under heating at around the boiling point of the solvent.

4. Process according to claim 1, wherein the Lewis acid is aluminum chloride.

5. Process according to claim 1, wherein the final product is 1,1-dimethyl-3-(5-t-butyl-3-isoxazolyl)urea.

6. Process according to claim 1, wherein the amount of the carbamoyl halogenide to the starting amine is about 1.0 to about 1.2 molar equivalent.

7. Process according to claim 1, wherein ratio of the Lewis acid to the starting amine is about 1.0 to about 1.2 molar equivalent.